(12) United States Patent
Riley et al.

(10) Patent No.: US 8,524,971 B2
(45) Date of Patent: Sep. 3, 2013

(54) CATALYST FOR HIGHER PRODUCTION RATES IN HYDROCARBON DEHYDROGENATION

(75) Inventors: Mark G. Riley, Hinsdale, IL (US); Bipin V. Vora, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 570 days.

(21) Appl. No.: 12/406,522

(22) Filed: Mar. 18, 2009

(65) Prior Publication Data
US 2010/0240941 A1    Sep. 23, 2010

(51) Int. Cl.
*C07C 5/333*    (2006.01)

(52) U.S. Cl.
USPC ........... 585/660; 585/634; 585/635; 585/654; 585/659

(58) Field of Classification Search
USPC .......................... 585/654, 659, 660, 634, 635
See application file for complete search history.

(56) References Cited

U.S. PATENT DOCUMENTS

| | | | | |
|---|---|---|---|---|
| 2,921,102 A * | 1/1960 | Lowman | ...................... | 585/602 |
| 2,988,579 A * | 6/1961 | Watkins | ........................ | 585/635 |
| 3,484,498 A | 12/1969 | Berg | | |
| 3,652,231 A | 3/1972 | Greenwood et al. | | |
| 4,720,336 A * | 1/1988 | Vora et al. | ....................... | 208/46 |
| 5,030,338 A * | 7/1991 | Harandi et al. | ................ | 208/135 |
| 5,233,118 A * | 8/1993 | Bricker et al. | ................. | 585/660 |
| 5,723,707 A * | 3/1998 | Heyse et al. | .................... | 585/444 |
| 6,103,651 A | 8/2000 | Leitzel | | |
| 6,177,381 B1 | 1/2001 | Jensen et al. | | |
| 6,280,608 B1 * | 8/2001 | Jensen et al. | ................... | 208/143 |
| 6,472,577 B1 * | 10/2002 | Zimmermann et al. | ....... | 585/441 |
| 6,486,370 B1 | 11/2002 | Rende et al. | | |
| 6,617,481 B1 | 9/2003 | Kulprathipanja et al. | | |
| 6,670,516 B1 | 12/2003 | Marinangeli et al. | | |
| 6,709,640 B1 | 3/2004 | Romatier et al. | | |
| 6,734,245 B2 | 5/2004 | Baranek | | |
| 6,756,515 B2 * | 6/2004 | Rende et al. | ................... | 585/444 |
| 6,969,496 B2 * | 11/2005 | Vetter et al. | .................... | 422/221 |
| 7,241,376 B2 | 7/2007 | Gu et al. | | |
| 2004/0133054 A1* | 7/2004 | Pelati et al. | ..................... | 585/444 |
| 2005/0139515 A1* | 6/2005 | Gu et al. | .......................... | 208/46 |

OTHER PUBLICATIONS

Ginestra, Jean C., "Pinning of a Bed of Particles in a Vertical Channel by a Cross Flow of Gas", Ind. Eng. Chem. Fundam. 1985, 24, 121-138.

* cited by examiner

*Primary Examiner* — In Suk Bullock
*Assistant Examiner* — Bradley Etherton
(74) *Attorney, Agent, or Firm* — Arthur E Gooding

(57) ABSTRACT

A process is presented for the dehydrogenation of hydrocarbons in a radial flow reactor. The process includes the continuous feeding of catalyst into the reactor and the continuous withdrawal of catalyst from the reactor, where the catalyst is modified to increase the increased density. The catalyst is a layered structure with a dense core and an active catalytic outer layer.

18 Claims, No Drawings

CATALYST FOR HIGHER PRODUCTION RATES IN HYDROCARBON DEHYDROGENATION

FIELD OF THE INVENTION

The present invention relates to the production of olefins. In particular, this relates to an paraffin dehydrogenation process using a layered catalyst for improved efficiency in the paraffin dehydrogenation reactor.

BACKGROUND OF THE INVENTION

This invention relates to a layered catalyst, a process for making the catalyst and the use of the catalyst. The development of detergents has led to the development and use of alkylbenzene sulfonates. Initially branched alkylbenzene sulfonates were developed, but due to biodegradability issues, it was found that linear alkylbenzene sulfonates were found to biodegrade more rapidly, and processes for making linear alkylbenzene sulfonates (LABS) were developed.

The production of LABS begins with the reacting of benzene with linear olefin compounds, and which in turn are reacted with sulfonate compounds to produce the LABS. The reacting of benzene with linear olefins over a catalyst produces linear alkylbenzenes (LABs). Therefore the production of LAB is important, and the production of the precursors of benzene and linear olefins is important. LAB processes are described in the book edited by R. A. Meyers entitled "Handbook of Petroleum Refining Processes" (McGraw Hill, N.Y. 1986) and "Ullmann's Encyclopedia of Industrial Chemistry," Volumes A8 and A13, Fifth Edition (VCH, Weinheim, Germany). Flow schemes are illustrated in U.S. Pat. No. 3,484,498 issued to R. C. Berg, U.S. Pat. No. 3,494,971 issued to E. R. Fenske, U.S. Pat. No. 4,523,048 issued to Vora which teaches use of a selective diolefin hydrogenation zone, and U.S. Pat. No. 5,012,021 issued to B. Vora which teaches use of a selective monoolefin hydrogenation zone. Solid alkylation catalysts are illustrated in U.S. Pat. No. 3,201,487 issued to S. Kovach et al.; U.S. Pat. No. 4,358,628 issued to L. Slaugh; U.S. Pat. No. 4,489,213 issued to S. Kovach; and U.S. Pat. No. 4,673,679 issued to D. Farcasiu. Zeolitic solid alkylation catalysts are disclosed in U.S. Pat. No. 3,751,506; U.S. Pat. No. 4,387,259; and U.S. Pat. No. 4,409,412.

There are many byproducts during the process, and the production of linear alkylbenzene requires control and selective catalyst, as well as methods of recovering compounds that can be recycled, or routed to other reactors to increase the yield of LAB. The catalysts are specialized for selectivity and yields. Improvements in the catalyst can increase yields to meet increased demands for LAB.

SUMMARY OF THE INVENTION

A process for the dehydrogenation of a hydrocarbon stream in a radial flow reactor is presented. The process comprises flowing the hydrocarbon stream over a bed of catalyst in a moving bed. The catalyst is continuously fed into the moving bed reactor, where the bed resides in an annular region with the hydrocarbon stream flowing across the annular region, and the catalyst is continuously withdrawn from the moving bed reactor. The catalyst is designed to prevent pinning due to the increased flows of the hydrocarbon stream and comprises a layered catalyst having an inner core with a density of at least 2.7 g/cc, and an outer layer having a thickness between 30 micrometers and 150 micrometers.

In an alternate embodiment, the catalyst can be increased in size, where the inner core is at least 100 micrometers in diameter and preferably 300 micrometers in diameter.

Other objects, advantages and applications of the present invention will become apparent to those skilled in the art from the following detailed description.

DETAILED DESCRIPTION OF THE INVENTION

Increasing the production of LABs while controlling the process requires the adjustment of many variables. The increased production first requires an increase in the production of the precursors, such as the linear olefins. The olefins are produced by dehydrogenation of paraffins, and generally, the process is carried out as a batch process where the dehydrogenation of paraffins is performed over a fixed bed of catalyst, and when the catalyst activity is sufficiently degraded, the process is stopped, and the catalyst bed is replaced with new, regenerated catalyst.

While the control of the catalytic properties of the catalyst has been studied extensively, the mechanical properties have been left alone. The catalysis occurs in the outer most layers of the catalyst and a layered catalyst has been developed to utilize this feature by using a cheaper inert core for the catalyst particles. However, the chemistry of the catalysis has been studied, without addressing flow issues with respect to the mechanical aspects of the process and the interaction between the solid catalyst particles and the fluid reactants. The process has been adjusted to control flow and reaction conditions to improve yields based upon catalytic properties and contact times of the reactants with the catalyst, but not the mechanical properties of the catalyst, other than attrition resistance. Mechanical properties of the catalyst can have an influence on the control of flow conditions. Improvements in the control of the reaction can be effected by improvements in the mechanical aspects of the catalyst, namely the size of the particles, or the density of the particles. These improvements can broaden the operating ranges for many catalytic reactions.

Moving bed systems are common in hydrocarbon processing reactions. The moving bed system typically is a cross-flow system where the catalyst is added at the top, flows downward through an annular region, and is removed at the bottom of the reactor. The catalyst bed comprises particles that are held between a vertical and cylindrical inlet screen and a vertical and cylindrical outlet screen defining the reactor bed region. The fluid comprising the reactants flows substantially horizontally, in a radial direction, across the reactor bed.

In order to increase the utilization of the reactors, the flow of reactants is increased, and the operation conditions are often more severe then when the reactor was initially designed. The increase flow of reactants often is accompanied with the increased flow of catalyst. The horizontal flow of reactants through the bed of catalyst can slow the flow of catalyst particles, and can even cause particles to pin the particles on the screen. The pinning occurs when the frictional forces between the screen and the particles as imposed by the pressure of the fluid resist the downward motion of the particles. This problem can affect the operation of the reactor, as particles trapped against the screen prevent downward flow of catalyst particles and can create voids within the reactor bed. The voids are spaces in the reactor bed where catalyst particles can be fluidized and churn, thereby generating catalyst fines. Another problem is that pinned particles are not recycled for regeneration according to the flow and can have reduced activity or even deactivate entirely, thereby further reducing the efficiency of the reactor.

The operating conditions are designed to avoid the circumstances that lead to pinning. However, as flow conditions are increased to increase productivity with current reactors, pinning and the creation of voids occurs. When pinning occurs, the fluid flow rates in the reactor must be reduced until the catalyst begins flowing. In some cases, the process fluid flow must cease in order to get the catalyst moving again. This leads to significant interruptions in the process. Pinning can also be a significant problem for semi-continuous operation, where some catalyst is periodically added and withdrawn from the reactor. Therefore the catalyst experiences a static operating period, where the catalyst must overcome static friction with the screen when new catalyst is added and old catalyst is withdrawn from the reactor.

The production of olefins from paraffins is carried out through a dehydrogenation process. Dehydrogenatable hydrocarbons are contacted with a catalyst in a dehydrogenation reactor under dehydrogenation reaction conditions. The contacting is normally carried out on a fixed bed, but can be carried out in a reactor where the catalyst is continuously withdrawn and replaced with regenerated catalyst. This provides for a more continuous process with less down time than a fixed bed reactor. The fixed bed reactor requires periodic shutdown to replace the spent catalyst with regenerated catalyst.

The present invention provides for the production of olefins using a catalyst that can overcome the limitations due to pinning, and can increase the capacity of reactors currently in use. The olefins are produced from paraffins by dehydrogenation, where the paraffins have from 6 to 20 carbon atoms. The process is a hydrocarbon conversion process for the dehydrogenation of a hydrocarbon stream in a radial flow reactor. A hydrocarbon stream flows over a bed of catalyst in a moving bed reactor, where the catalyst is continuously fed into the moving bed reactor, and the catalyst is continuously withdrawn from the moving bed reactor. The catalyst comprises a layered structure having an inner core with a density of at least 2.55 g/cc, and an outer layer having a thickness between 30 micrometers and 150 micrometers. Preferably, the inner core density will be at least 2.7 g/cc. In another embodiment, the inner core density will be at least 3 g/cc. In another preferred embodiment, the inner core is at least 3.5 g/cc. The catalyst is fed continuously into the top of the reactor and withdrawn from the bottom of the reactor, where the catalyst flows down an annular region defining the catalyst bed. There is a relationship that when the size of the inner core increases, the minimum density can decrease, and when the size of the inner core decreases, the inner core density increases to allow the catalyst particle to overcome the resistance to movement, or pinning.

The outer layer of the catalyst can include an alkali component, alumina, and a noble metal. The noble metal is selected from one or more of the metals: palladium, iridium, ruthenium, rhodium, osmium, and platinum. The noble metal, when incorporated into the outer layer of the catalyst comprises from 0.05 to 5.0% by weight of the outer layer, with a preferred amount of the noble metal from 0.05 to 1% by weight of the outer layer. The alkali component can be an alkali or an alkaline earth element, and can include a combination of one or more of the alkali or alkaline earth elements. The alkali component are modifier metals and include lithium, sodium, potassium, rubidium, cesium, beryllium, magnesium, calcium, strontium, and barium. Preferred modifier metals are alkali metals and include lithium, sodium, potassium, rubidium, and cesium. The modifier metal is in an amount from 0.1 to 5% by weight of the outer layer, with a preferred amount from 0.25 to 2.5% by weight of the outer layer.

The catalyst can further comprise at least one promoter metal distributed over the outer layer, and preferably uniformly dispersed. The promoter metals are selected from the group comprising gallium, indium, germanium, tin, lead, bismuth, rhenium, cerium, zinc, and combinations thereof. Preferably the promoter metal is tin. The promoter metal, when incorporated into the outer layer of the catalyst comprises from 0.1 to 2 wt. % of the outer layer, and preferably from 0.1 to 1 wt. % of the outer layer.

The catalyst has an inner core of an inert material that is selected from one or more of the following metal oxides: aluminas, zirconia, hafnia, zirconia, niobia, tantalum oxide, tungsten oxide, molybdenum oxide, titania, vanadia, tin oxides, lead oxides, antimony oxides, bismuth oxides, copper oxides, chromium oxides, molybdenum oxides, manganese oxides, iron oxides, cobalt oxides, and nickel oxides. Other dense materials, including clays can be used in the inner core and include cordierite, kaolinite, kaolin, saponite, mullite, olivine, spinel, kyanite, silicas, silicon nitrides, silicon carbide, magnesia, and fosterite. In addition, materials can be combined, or clays or ceramic type materials can be combined with heavier metals or metal oxides to increase the density of the inner core. Some of the inner core materials are also not substantially penetrated by liquids, and preferably the inner core is non-porous. The materials which form the inner core can be formed into a variety of shapes such as pellets, extrudates, spheres, or irregularly shaped particles, although not all materials can be formed into each shape. Preparation of the inner core can be done by means known in the art such as oil dropping, pressure molding, metal forming, pelletizing, granulation, extrusion, rolling methods, and marumerizing. A spherical inner core is preferred. The inner core whether spherical or not has an effective diameter of 0.05 mm (0.0020 in) to 5 mm (0.2 in) and preferably from 0.8 mm (0.031 in) to 3 mm (0.12 in). For a non-spherical inner core, effective diameter is defined as the diameter the shaped article would have if it were molded into a sphere. Once the inner core is prepared, it is calcined at a temperature of from 400° C. (752° F.) to 1800° C. (3272° F.). When the inner core comprises cordierite, it is calcined at a temperature of from 1000° C. (1832° F.) to 1800° C. (3272° F.).

The production of olefins from paraffins is endothermic, and the addition of heat facilitates the control of the reaction, and moving the reaction forward. The process can include the addition of a solid inert material for the transport of heat into the reactor, where the solid inert heat carrier is heated outside the reactor to a temperature at or above the reaction temperature and transported into the reactor. The heat from the heat carrier facilitates maintaining the temperature of the reactor. This process is also applicable to any moving bed reactor such as a fluidized bed reactor.

The process utilizes the increased density of the catalyst to prevent holdups. The reactive part of the catalyst cannot be made more dense, as this would change the properties of the catalyst, and the catalyst would not perform as desired. For example, increasing the density of the outer layer will generally reduce the pore volume of the catalyst and make the catalyst less effective. Other aspects of changing the density of the catalytically active part can be a reduction in pore diameter, or reduction in surface area. These are significant drawbacks that one wants to avoid. Therefore, the outer layer remains substantially unchanged in the process, but the inner core is altered to produce the desired properties.

The process can also used with transport reactors, which are common in hydrocarbon processing. In a transport reactor, the catalyst bed moves through the reactor when the catalyst contacts the hydrocarbon feedstream. This is different from fixed bed reactors where the catalyst doesn't move, or ebullated bed reactors where the catalyst particles circulate within the reactor, but are not carried out of the reactor. In a transport reactor, the catalyst is carried through the reactor by the reactants passing through the reactor, or the catalyst is transported through the reactor while the reactants flow over the catalyst, such as in a radial flow reactor. Although the general direction for a transport reactor is in the upward direction, a riser reactor, it can also be downward, horizontal, or at some angle between vertical and horizontal. Fluidized bed reactors are also possible where the catalyst can have a residence time within the reactor, but is carried out at a different rate than the effluent stream. The catalyst would be withdrawn continuously from the reactor, and regenerated in a regeneration unit.

In a dehydrogenation process, the paraffin feed is preheated to the desired reaction temperature and passed into the dehydrogenation reactor containing the catalyst. The reactor may contain one or more zones where the catalyst flows from one zone to the next, and is continuously withdrawn at the bottom of the reactor, while fresh regenerated catalyst is introduced to the reactor at the top of a first reaction zone. A radial flow reactor is preferred, where the hydrocarbon stream flows across a catalyst bed that is slowly moving down the reactor. The hydrocarbon may be in the liquid phase, a mixed vapor-liquid phase or the vapor phase when it contacts the catalyst. Preferably, it is in the vapor phase.

Hydrocarbons which can be dehydrogenated include hydrocarbons with 2 to 30 or more carbon atoms including paraffins, isoparaffins, alkylaromatics, naphthenes and olefins. A preferred group of hydrocarbons is the group of normal paraffins with 2 to about 30 carbon atoms. For the production of LABs, the preferred normal paraffins are those having 8 to 25 carbon atoms.

Dehydrogenation conditions include a temperature of between 400° C. and 900° C., a pressure of between 1 kPa and 1013 kPa and a liquid hourly space velocity (LHSV) between 0.1 and 100 $hr^{-1}$. Generally for normal paraffins, the lower the molecular weight the higher the temperature required for comparable conversion. The pressure in the dehydrogenation zone is maintained as low as practicable, consistent with equipment limitations, to maximize the chemical equilibrium advantages.

The effluent stream from the dehydrogenation zone generally will contain unconverted dehydrogenatable hydrocarbons, hydrogen and the products of dehydrogenation reactions. This effluent stream is typically cooled and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions or by means of a suitable fractionation scheme. Unconverted dehydrogenatable hydrocarbons are recovered and may be recycled to the dehydrogenation zone. Products of the dehydrogenation reactions are recovered as final products, or as intermediate products in the preparation of other compounds, such as LABs.

In another embodiment, the invention comprises a hydrocarbon conversion process for the dehydrogenation of a hydrocarbon stream in a radial flow reactor. The process entails flowing a hydrocarbon stream over a bed of catalyst in a moving bed reactor, and continuously feeding catalyst into the moving bed reactor and withdrawing catalyst from the reactor. The catalyst comprises a layered structure, wherein the catalyst is sufficiently large in diameter to overcome the frictional forces that lead to pinning. The catalyst comprises a layered structure having an inner core with a particle diameter greater than 100 micrometers, and an outer layer of active catalytic material having a thickness between 30 micrometers and 150 micrometers. The inner core can be sized between 100 micrometers and 3 millimeters, and preferably between 0.3 millimeters and 0.8 millimeters.

The inner core material can be made of any inert material such as metal oxides, or other ceramic compounds. The limitations on materials are due to small particles having too low a density, such that when sized sufficiently small, the particles are subject to pinning. This is overcome by increasing the density of the particles, or increasing the size of the particles.

In another embodiment, the process comprises flowing a hydrocarbon stream over a bed of catalyst in a moving bed reactor, and continuously feeding catalyst into the moving bed reactor and withdrawing catalyst from the reactor. The catalyst in the process comprises a layered structure wherein the catalyst has a bulk density of at least 0.78 g/cc. Preferably, the bulk density is greater than 0.8 g/cc. The layered structure includes an inner core and an outer layer having a thickness between 30 micrometers and 150 micrometers. The inner core is comprised of an inert material having a relatively high density and can be one or more materials selected from zirconia, hafnia, zirconia, niobia, tantalum oxide, tungsten oxide, molybdenum oxide, titania, vanadia, tin oxides, lead oxides, antimony oxides, bismuth oxides, copper oxides, chromium oxides, molybdenum oxides, manganese oxides, iron oxides, cobalt oxides, and nickel oxides.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A hydrocarbon conversion process for dehydrogenation of a hydrocarbon stream in a radial flow reactor, comprising:
    flowing the hydrocarbon stream, comprising paraffins having from 6 to 20 carbon atoms, in a moving bed reactor over a bed of catalyst;
    continuously feeding catalyst into the moving bed reactor;
    adding a solid inert heat carrier with the catalyst to the reactor; and
    continuously withdrawing the catalyst from the moving bed reactor, wherein the catalyst comprises a layered structure, having an inner core with a density of at least 2.55g/cc, and an outer layer having a thickness between 30 micrometers and 150 micrometers.

2. The process of claim 1 wherein the moving bed reactor is a radial flow reactor, and the catalyst is fed into the top of the radial flow reactor and withdrawn from the bottom of the reactor.

3. The process of claim 1 further comprising adding a solid inert heat carrier having a density less than the catalyst.

4. The process of claim 1 wherein the catalyst inner core consists of an inert material selected from the group consisting of zirconia, hafnia, zirconia, niobia, tantalum oxide, tungsten oxide, molybdenum oxide, titania, vanadia, tin oxides, lead oxides, antimony oxides, bismuth oxides, copper oxides, chromium oxides, molybdenum oxides, manganese oxides, iron oxides, cobalt oxides, nickel oxides, cordierite, kaolinite, kaolin, saponite, mullite, olivine, spinel, kyanite, aluminas, silicas, silicon nitrides, silicon carbide, magnesia, fosterite, and mixtures thereof.

5. The process of claim 1 wherein the catalyst comprises a promoter metal selected from the group consisting of gallium, indium, germanium, tin, lead, bismuth, rhenium, cerium, zinc, and mixtures thereof.

6. The process of claim 1 wherein the outer layer of the catalyst comprises an alkali component, alumina, and a noble metal component selected from the group consisting of palladium, iridium, ruthenium, rhodium, osmium, platinum and mixtures thereof.

7. The process of claim 6 wherein the noble metal is platinum.

8. A hydrocarbon conversion process for dehydrogenation of a hydrocarbon stream in a radial flow reactor, comprising:
   flowing the hydrocarbon stream, comprising paraffins having from 6 to 20 carbon atoms, in a moving bed reactor over a bed of catalyst;
   continuously feeding catalyst into the moving bed reactor;
   adding a solid inert heat carrier with the catalyst to the reactor; and
   continuously withdrawing the catalyst from the moving bed reactor, wherein the catalyst comprises a layered structure, having an inner core having a particle diameter greater than 100 micrometers, and an outer layer having a thickness between 30 micrometers and 150 micrometers.

9. The process of claim 8 wherein the moving bed reactor is a radial flow reactor, and the catalyst is fed into the top of the radial flow reactor and withdrawn from the bottom of the reactor.

10. The process of claim 8 further comprising adding a solid inert heat carrier having a density less than the catalyst.

11. The process of claim 8 wherein the catalyst inner core consists of an inert material selected from the group consisting of zirconia, hafnia, zirconia, niobia, tantalum oxide, tungsten oxide, molybdenum oxide, titania, vanadia, tin oxides, lead oxides, antimony oxides, bismuth oxides, copper oxides, chromium oxides, molybdenum oxides, manganese oxides, iron oxides, cobalt oxides, nickel oxides, cordierite, kaolinite, kaolin, saponite, mullite, olivine, spinel, kyanite, aluminas, silicas, silicon nitrides, silicon carbide, magnesia, fosterite, and mixtures thereof.

12. The process of claim 11 wherein the catalyst comprises a promoter metal selected from the group consisting of gallium, indium, germanium, tin, lead, bismuth, rhenium, cerium, zinc, and mixtures thereof.

13. The process of claim 8 wherein the outer layer of the catalyst comprises an alkali component, alumina, and a noble metal component selected from the group consisting of palladium, iridium, ruthenium, rhodium, osmium, platinum and mixtures thereof.

14. The process of claim 13 wherein the noble metal is platinum.

15. A hydrocarbon conversion process for dehydrogenation of a hydrocarbon stream in a radial flow reactor, comprising:
   flowing the hydrocarbon stream, comprising paraffins having from 6 to 20 carbon atoms, in a moving bed reactor over a bed of catalyst;
   continuously feeding catalyst into the moving bed reactor;
   adding a solid inert heat carrier to the reactor; and
   continuously withdrawing the catalyst from the moving bed reactor, wherein the catalyst has a bulk density of at least 0.78 g/cc, and comprises a layered structure, having an inner core and an outer layer having a thickness between 30 micrometers and 150 micrometers.

16. The process of claim 15 wherein the catalyst inner core consists of an inert material selected from the group consisting of zirconia, hafnia, zirconia, niobia, tantalum oxide, tungsten oxide, molybdenum oxide, titania, vanadia, tin oxides, lead oxides, antimony oxides, bismuth oxides, copper oxides, chromium oxides, molybdenum oxides, manganese oxides, iron oxides, cobalt oxides, nickel oxides, cordierite, kaolinite, kaolin, saponite, mullite, olivine, spinel, kyanite, aluminas, silicas, silicon nitrides, silicon carbide, magnesia, fosterite, and mixtures thereof.

17. The process of claim 15 wherein the outer layer of the catalyst comprises an alkali component, alumina, and a noble metal component selected from the group consisting of palladium, iridium, ruthenium, rhodium, osmium, platinum and mixtures thereof.

18. The process of claim 15 wherein the catalyst comprises a promoter metal selected from the group consisting of gallium, indium, germanium, tin, lead, bismuth, rhenium, cerium, zinc, and mixtures thereof.

* * * * *